United States Patent [19]

Riddell

[11] Patent Number: 4,623,334
[45] Date of Patent: Nov. 18, 1986

[54] INTRAVENOUS DRUG INFUSION APPARATUS

[75] Inventor: James G. Riddell, Belfast, Northern Ireland

[73] Assignee: Vanderbilt University, Nashville, Tenn.

[21] Appl. No.: 723,215

[22] Filed: Apr. 15, 1985

Related U.S. Application Data

[63] Continuation-in-part of Ser. No. 472,926, Mar. 7, 1983, abandoned.

[51] Int. Cl.⁴ .............................. A61M 37/00
[52] U.S. Cl. ............................. 604/85; 604/56; 604/246
[58] Field of Search .............. 604/56, 80-83, 604/85, 245, 246, 410, 122; 128/DIG. 3

[56] References Cited

U.S. PATENT DOCUMENTS

| | | | |
|---|---|---|---|
| 1,655,664 | 1/1928 | Russell | 604/85 |
| 3,254,647 | 6/1966 | Vogel | 604/85 |
| 3,343,538 | 9/1967 | Morley | 604/122 |
| 4,258,723 | 3/1981 | McCue et al. | 604/56 |
| 4,259,952 | 4/1981 | Avoy | 604/82 |
| 4,267,837 | 5/1981 | Purdy et al. | 604/245 |
| 4,424,056 | 1/1984 | Urquhart et al. | 604/85 |

OTHER PUBLICATIONS

*Journal of Phar. Sci.*, vol. 57, No. 6, Jun. 1968, Loo et al., "New Method for Calculating the Intrinsic Absorption Rate of Drugs", pp. 918-928.
*Am. Heart J.*, vol. 102, No. 5, Nov. 1981, Starget et al., "Clin. Comp. of Rapid Infusion and Multiple Injection Methods for Lidocaine Loading" pp. 872-876.
*J. of Pharm. Exp. Thera.*, vol. 150, 1965, Foulkes, "On the Mechanism of Chlorothiazide-Induced Kaliuresis in the Rabbit" pp. 406-413.
Boyes et al., J. Pharm. & Exper. Ther., 174:1-8 (1970).
Salzer et al., Clin. Pharmacol. Ther., 29(5):617-623 (1981).

*Primary Examiner*—C. Fred Rosenbaum
*Assistant Examiner*—Michelle N. Lester
*Attorney, Agent, or Firm*—Tilton, Fallon, Lungmus & Chestnut

[57] ABSTRACT

An intravenous drug administration apparatus is provided which automatically delivers a drug with an exponentially decreasing concentration from a high loading concentration down to a patient maintenance concentration followed by continued infusion at the maintenance concentration rate. The apparatus includes a large container, such as an intravenous solution bag, which holds the low maintenance concentration, and a smaller vessel containing the high loading concentration. The low concentration solution is passed from the large volume container into the lower end of the smaller vessel so as to obtain a continuous mixing action within the vessel, and the mixed and progressively diluted solution is continuously removed from the vessel for delivery and infusion to the patient. The inlet to the vessel may be provided by a short length hypodermic needle and the outlet by a long length hypodermic needle which extends into the upper portion of the vessel. This apparatus has been found highly effective for the delivery of lidocaine, an antiarrhythmic drug.

12 Claims, 2 Drawing Figures

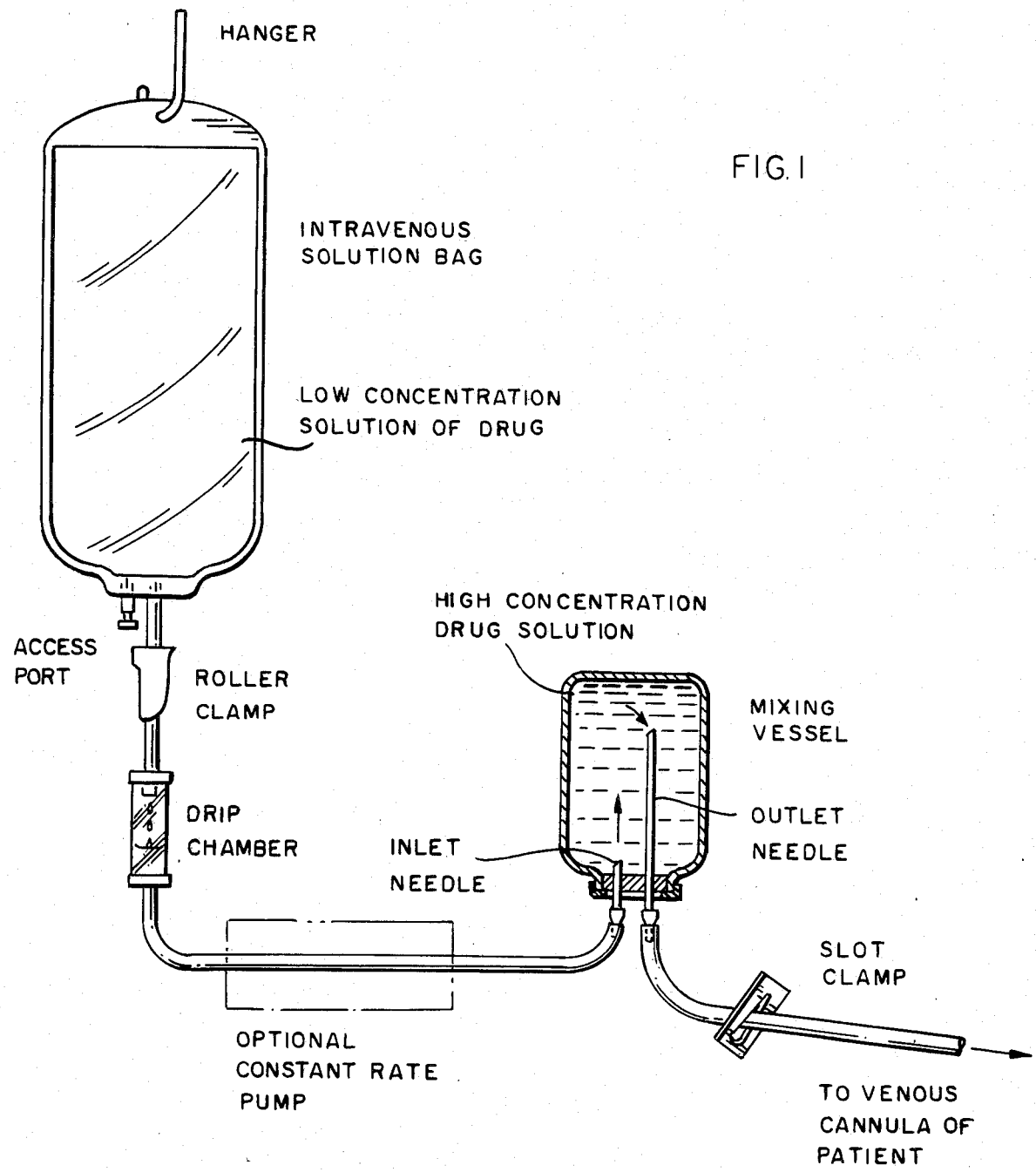

INTRAVENOUS DRUG INFUSION APPARATUS

GRANT REFERENCE

Experimental work relating to this invention was supported in part by grants from the United States Public Health Service: GM 15431, AG 01395, and 5MOIRR95.

RELATED APPLICATION

This application is a continuation-in-part of copending application Ser. No. 472,926, filed Mar. 7, 1983, now abandoned.

BACKGROUND AND PRIOR ART

Intravenous solutions, such as saline or glucose solutions, are often used as carriers for the continuous administration of drugs to patients at controlled infusion rates. The drugs may be prepackaged in intravenous solution bags or bottles. The drug-containing intravenous solution may be administered by gravity flow, using a drip chamber and rate control valve, or a drop chamber with automatic rate controller. Infusion pumps may also be employed which can be preset to provide a constant solution volume delivery rate, and thereby a selected rate of the drug dissolved in the intravenous solution at a preestablished concentration.

A constant rate drug infusion apparatus, as described above, is not a clinically adequate administration means for drugs where rapid achievement of therapeutic level is needed followed by the maintenance of a highly critical serum level to obtain therapeutic effectiveness over a long period of administration without adverse side effects. Bolus injections of the drug can be used to provide a rapid serum concentration followed by a constant rate infusion, but the transition period between the loading injection and the achievement of a stable serum level at the desired therapeutic concentration is not effectively controlled. A rapid injection followed by a constant slow rate infusion has the disadvantage that there is a considerable time during the early hours when the plasma concentrations are subtherapeutic. A staged infusion has therefore been proposed and used to some extent, a fast constant infusion being used following the loading injection, and then by a slow constant infusion. Multiple further rapid injections may also be used to augment a slow constant infusion. All of these procedures have the disadvantages that they require attention at strictly defined times if the plasma concentration is not to rise to a toxic level or to a level giving undesired side effects, or, on the other hand, to fall to a subtherapeutic level.

When a drug is administered intravenously the early plasma drug concentrations are much higher than the drug concentrations in tissues with a poor blood supply. With time the drug distributes to these other tissues and a steady state of distribution is reached. Once this distribution in the body has reached steady state, the aim is to maintain the steady state by infusing drug at the same rate at which it is eliminated from the body. It has been known for some time that the ideal infusion regimen to achieve and maintain constant plasma concentrations of a drug is a loading dose followed by an infusion which falls exponentially in concentration to that required to maintain a steady state. See Kruger-Thiemer (1968) *Europ. J. of Pharmacology*, 4:317. Heretofore, however, there has been no simple practical method of producing this infusion regimen.

The problem of optimized intravenous drug administration has been particularly studied in connection with the infusion of anti-arrhythmic drugs such as lidocaine. The effectiveness of lidocaine depends on the rapid achievement and maintenance of rather narrow therapeutic plasma levels, viz. 1.5 to 5.5 micrograms/milliliter. Concentrations above the critical range have been associated with toxic effects including convulsions, coma, and respiratory arrest, while lower concentrations do not adequately protect the patient against a life-threatening arrhythmia. See Salzer, et al., *Clin. Pharmacol. Ther.*, 29 (5) 617-624 (1981); and Stargel, et al., *Amer. Heart J.* 102 872-876 (1981). The ideal exponentially decreasing infusion between a loading injection and the constant rate infusion has been approximated by using mechanical constant rate infusion pumps and stepped decreases in the delivery rate. See Vaughn, et al. *Europ. J. Clin. Pharmacol.* 10, 433-440; and Loo, et al., *J. Pharm. Sci.*, 57, 918-928 (1968).

An additional method using mechanical mixer for achieving an exponentially decreasing delivery has been tested in dogs: Boyes, et al., *J. Pharmacol. Exp. Ther.* (1970), 174, 1-8. For a similar experimental apparatus, see Foulkes, *J. Pharmacol. Exp. Ther.* (1965) 150, 406-413. As described in these references, an intravenous solution containing no drug is used for progressive dilution of a solution containing the drug. The solutions were mixed mechanically, viz. by a mixer or magnetic stirrer.

Boyes, et al. pointed out with reference to apparatus for exponentially decreasing infusion of lidocaine that "this is probably not practical in a clinical situation." *Clinical Pharmacol. and Therap.* (1971) 12: 105-116. Similarly, Tsuei et al, writing about the design of regimens to achieve and maintain a predetermined plasma drug level range, stated that: "The practial difficulties in giving an exponential intravenous infusion preclude the use of these approaches [Bolus dose with exponentially decreasing rate to constant rate] in everyday clinical situations."*Clinical Pharm. & Therap.* (1980) 28: 289-295, at 291.

SUMMARY OF INVENTION

The intravenous drug administration apparatus of this invention provides in a simple and automatic manner a first administration phase in which the drug is infused at an exponentially decreasing concentration from a high loading concentration down to a maintenance concentration, and a second phase in which there is continued delivery of the low maintenance concentration. Observation and resettings are minimized. The patient may be given one or more loading injections, such as for the administration of lidocaine as anti-arrhythmic drug, and then the infusion is started to automatically provide the exponentially decreasing phase during the transitional period while the drug is distributing from the blood into the tissues, and thereafter the maintenance concentration being adequate to replace the drug as it is eliminated from the body.

The apparatus includes a closed container with a first sterile intravenously administerable carrier containing the drug at a low patient maintenance concentration. There is also a closed rigid mixing vessel of smaller volume having a second sterile intravenously administerable carrier containing the drug at a high loading concentration. The smaller vessel functions as a mixing vessel, and is provided with inlet and outlet means constructed and arranged to provide a mixing action within the vessel. The inlet is connected to the larger volume low concentration carrier, and the outlet to the infusion cannula connected to the patient. In a preferred arrangement, hypodermic needles are employed to provide the inlets and outlets for the mixing vessel. No mechanically operated mixing device is required. The construction and arrangement of the mixing vessel inlet and outlet means providing the only mixing action associated with the vessel.

In a preferred application, the drug in the solutions of the apparatus is lidocaine. However, the apparatus is adaptable for use with many other drugs which are capable of being administered intravenously in aqueous solutions or emulsions.

In commercial embodiments of the apparatus of this invention, it is preferred to have the drug prepackaged in both the intravenous solution bag and in the mixing vessel. Further, the mixing vessel may be provided in the form of a vial equipped with a previously described inlet and outlet hypodermic needle. Closure caps may be provided for the projecting ends of the needles, which can be removed to permit their attachments to the appropriate conduits. Both the bag and the mixing vessel may be supplied as components of a complete intravenous administration set.

THE DRAWING

The apparatus of this invention is shown in an illustrative embodiment in FIG. 1 of the attached drawing. It should be understood that certain of the components of the apparatus are shown diagramatically because of their well-known construction, and that the relative size of the apparatus components, such as the solution bag and the mixing vessel, can be varied widely and are not necessarily shown to scale in the drawing. FIG. 2 illustrates a mixing vessel of modified design which can also be used as a package for the high concentration drug in an aqueous carrier.

DETAILED DESCRIPTION

The intravenous drug administration apparatus of this invention utilizes as one of its components a closed container with a first sterile intravenously administerable aqueous solution therein. This container may be a standard intravenous solution bag or bottle containing 0.5 or 1.0 liters of an intravenous solution, such as a normal saline solution, a glucose solution, etc.

The drug to be administered is incorporated in the intravenous solution at a low maintenance concentration. For example, the drug may be lidocaine dissolved in the amount of 2,000 mg in 1,000 ml of normal saline, giving a concentration of 2 mg/ml. Other anti-arrhythmic drugs such as mexiletine, disopyramide, bretylium, flecainide, and procainamide can be administered. Drugs for other conditions can be advantageously infused in the same manner. For example, the apparatus may be used for the administration of hyponotic anaesthetic agents such as methohexitone, disoprofol, or midazolam; an analgesic agent such as alfentanyl; a respiratory stimulant such as doxapram; a drug for premature labor such as ritodrine or salbutamol; and drugs for acute asthmatic attacks such as aminophylline, salbutamol and terbutaline.

The large volume container providing a solution of the drug at the low maintenance concentration will have an outlet positionable at the bottom thereof for gravity outflow, as is well known with respect to intravenous solution bags and bottles. The container may also be provided with an inlet port for introduction of the drug, or the drug may be prepackaged in the container.

The apparatus also includes a closed rigid mixing vessel of smaller volume having a second sterile intravenously administerable aqueous carrier providing a high loading concentration of the drug. Typically, the intravenous carrier will be the same as that in the larger volume container, that is, it will be a saline solution, a glucose solution, etc., and the same drug will be dissolved or emulsified in the second solution, but at a considerably higher concentration. This higher concentration will correspond with the desired high loading concentration of the drug for an initial infusion. For example, where the drug is lidocaine and a normal saline solution is used, the mixing vessel and the solution therein may have a volume of 20 ml and may contain 200 mg lidocaine, giving a concentration of 10 mg/ml. As stated above, the larger volume container may have a lidocaine concentration of about 2 mg/ml. It will be understood that the relative concentrations and relative volumes of the first and second solutions are subject to wide variations, depending on the particular drug being administered, and the desired length of the period of administration. However, in general, the loading concentration in the second solution will be at least two to three times that of the maintenance concentration in the first solution, and the volume of the first solution will be at least five times that of the second solution.

The mixing vessel is provided with an inlet connected to the container outlet by conduit means, and the inlet means is designed to provide a solution mixing action within the vessel. The vessel is also provided with outlet means positioned and arranged with respect to the inlet means so that mixing of the solutons can occur within the vessel for discharging an admixed solution to the outlet. A delivery conduit is connected to the outlet for intravenous delivery of the admixed progressivly diluted solution to a patient during a first phase of the administration. In the second phase, with the continued administration of the maintenance solution no mixing dilution is needed. The concentration of the drug in the solution of the mixing vessel is at the same level as that of the larger volume container.

The apparatus can be operated entirely by gravity flow. The container with the low concentration drug is positoned at a higher level than the mixing vessel, and the solution is permitted to flow therefrom and into the mixing vessel under the action of gravity. However, it may be desirable to employ a constant rate pump. The pump may be preset to a desired flow rate, and interposed between the container and the mixing vessel. The low concentration solution is delivered from the outlet side of the pump to the mixing vessel. Suitable pumps are commercially available.

Other standard components of intravenous administration sets will preferably be included. For example, a drip chamber and a rate control clamp, such as a roller clamp, may be used in the conventional manner. Other commonly employed devices can be used, such as automatic rate controllers to assure the maintenance of a constant drip rate. There can also usually be provided a shut-off clamp on the downstream conduit between the mixing vessel and the cannula attached to the patient.

A representative assembly of the components referred to above, including those especially adapted for performing the method of the present invention, are shown in the accompanying drawing. FIG. 1 is shown in somewhat diagrammatic form and it should be understood that the components are not to exact scale. The intravenous solution bag, as shown, which contains the low concentration solution of the drug, is provided with a hanger for mounting it at a level above the mixing vessel to provide for gravity flow between the solution bag and the mixing vessel. In the illustration given, the bag has a lower outlet tube connecting to a drip chamber, which in turn is connected to the inlet of the mixing vessel by a conduit. A roller clamp may be used to provide for the drip rate adjustment. The lower end of the solution bag is also provided with an access port tube through which a drug may be introduced into the intravenous solution within the bag. Preferably, however, the drug is prepackaged, in which case an access port will not be needed.

As shown in FIG. 1, a conventional drip chamber is provided below the intravenous solution bag and connected by a conduit to the mixing vessel. The roller clamp may be mounted on the conduit adjacent the drip chamber for adjusting the drip rate, and thereby predetermining the constant flow rate. Alternatively, as described above, an automatic controller can be used. Further, as indicated by the dotted lines, a constant rate pump may be interposed in the conduit for passing the solution into the mixing vessel at a constant preset rate.

The mixing vessel will contain the sterile aqueous soluton of the drug at a high concentration corresponding to the desired loading concentration. In the illustration given, the mixing vessel consists of a small bottle or vial, having a rubber closure plug through which extend two hollow needles, a short inlet needle and a long outlet needle. The plug with the needles frictionally held therein is secured in the neck of the vial by means of a metal clamping ring. The needles may comprise commercially available standard hypodermic needles, or special mixing needles may be designed for this application. The inlet needle, as shown, terminates in the lower portion of the mixing vessel, while the outlet needle extends into and receives solution from the upper portion of the vessel. With this arrangement, mixing action occurs within the vessel. The solution introduced through the inlet needle enters as a jet stream to provide mixing and turbulence within the vessel. Since the ends of the inlet and outlet needles are separated, mixing can occur within the vessel, so that an admixed solution is discharged through the outlet needle. The outer end of the outlet needle is connected to a conduit for delivery to the venous cannula of the patient. As shown, a slide clamp is mounted on the outlet conduit, which may be moved from an open position to a clamping position cutting off the flow.

The mixing vessel, such as the one shown in FIG. 1, should be of rigid construction, for example, it may be formed of glass or a rigid plastic. It is also important to employ a needlelike inlet tube to promote turbulent mixing within the vessel. Another important feature is the physical separation between the points of fluid introduction and removal, that is, ends of the inlet and outlet tubes should be spaced apart within the mixing vessel. While it is advantageous to use a hypodermic needle to form the outlet, the outlet is less critical than the inlet and the spacing of the outlet from the inlet. With these features, low pressures and low flow rates can be employed to provide continuous administration of the drug for several hours.

In FIG. 2 there is shown a modified design of a mixing vessel. The container 10 may be formed of blow-molded plastic of sufficient thickness to impart rigidity to the walls of the vessel. A lid or closure 11 may be heat-sealed to the open top of vessel 10. Typical volumes of the vessel may range from 20 to 50 ml. For most applications, it is believed that either a 20 ml or 50 ml size will be appropriate.

Closure 11 may be provided with an integrally molded nipple or ferrule 15 to serve as an inlet. Similarly, the lower wall of vessel 10 may be provided with an integrally molded nipple 12 to serve as an outlet. To provide for a turbulent introduction of the lower concentration carrier, the shank or hub 16 of a hypodermic needle may be sealingly fitted inside the inlet tube 15, as shown in FIG. 2. The needle portion 17 extends into the interior of the vessel. The hypodermic needle gauge is preferably gauge 27 or smaller in order to provide for a jet-type introduction of the low concentration carrier into the vessel 10. The hub 13 of another hypodermic needle may be sealingly embedded in outlet tube 13, as shown in FIG. 2, with the needle portion 14 thereof extending at an angle away from the terminal end of the inlet needle 17. The outlet needle as shown is of a larger gauge than the inlet needle.

Where the vessel of FIG. 2 is used as a prepackaged container for the high concentration drug, the outer ends of the tubes 12 and 15 should be closed respectively by rupturable plastic sealing members 12a and 15a. For example, seal 12a may be applied, the vessel 10 completely filled with a high concentration solution or emulsion of the drug, and then seal 15a applied, such as by heat sealing. These seals can be pierced by an sharp instrument for connection of the prepackaged drug into the administration set. The arrangement will be similar to that illustrated in FIG. 1.

With the apparatus as shown in FIG. 1, after the patient has been given one or more injections of the drug to produce immediate loading, the slide clamp may be opened to permit the beginning of the infusion. At the start of the infusion, the drug will be administered at the high concentration of the mixing vessel. As the administration proceeds, the low concentration solution from the bag will progressively mix with and dilute the solution in the mixing vessel, thereby providing a close approximation to an exponentially reducing concentration as delivered to the patient. Since the volume of solution in the bag is much greater than that in the mixing vessel, a condition will be reached at which there is remaining solution in the bag, while the concentration of the solution in the mixing vessel is the same as that of the bag. Thereafter, the continued administration will be at the low maintenance concentration of the bag solution. During all phases of the administration, there will be a minimal need to monitor or attend the administration apparatus. The transitional infusion with exponentially reducing concentration and the continued infusion thereafter at the maintenance rate will be achieved automatically.

In an illustrative embodiment, a one liter intravenous solution bag containing 0.9% saline can be used. 10 ml lidocaine HCL (200 mg/ml) is introduced into the bag by an additive syringe, resulting in a lidocaine HCL concentration of 2 mg/ml (1.7 mg/ml lidocaine). The mixing vessel can consist of a 20 ml vial or prepackaged lidocaine solution containing 200 mg lidocaine HCL (8.7 mg/ml lidocaine). The vial may have a rubber closure through which hypodermic needles are inserted. The vial closure is pierced with two needles, the needle providing the inlet being ½"×27 SWG hypodermic needle, and the outlet being provided by a 1½"×22 SWG hypodermic needle. The inlet needle terminates in the lower portion of the inverted container, and the outlet needle extends into the upper portion, in the manner illustrated in FIG. 1. Preferably, although not essentially, the mixing vessel is completely full of solution, thereby eliminating any air space which might create air bubbles in the infusion solution. Alternatively the mixing vessel of FIG. 2 may be used.

In a delivery rate experiment, a constant rate pump was interposed in the conduit between the solution bag and the mixing vessel. The dye indocyanine green was substituted for the lidocaine at the same concentrations. The pump was set to deliver solution at a rate of 1 ml/min. As the solution jetted into the mixing vessel through the inlet needle, a mixing action was created, and mixed solution was continuously removed at the same rate through the outlet needle. The dye concentration as determined spectrophotometrically fell from 10 mg/ml to the concentration of 2 mg/ml by a close approximation to a predicted exponential reduction curve. After 15 minutes the concentration of the delivered solution had fallen to a 5.6 mg/ml (predicted (5.8), after 30 minutes to a 2.3 mg/ml (predicted 2.4), after 90 minutes to 2.0 mg/ml (predicted 2.1), and after 120 minutes continued at 2.0 mg/ml (predicted 2.0 mg/ml).

In use of the apparatus, total delivery time will depend on the volume of the low concentration solution. For example, with a 1 liter volume and a flow rate of 1 ml/min infusion can run for approximately 16.7 hours. At the same rate with a low concentration solution volume of 0.5 liters, the infusion can be continued for approximately 8.3 hours.

Where an initial loading dose is desired of higher concentration than that provided in the mixing vessel, an additional inlet (not shown) may be provided into the intravenous tubing between the mixing vessel and the cannula to the patient. At the beginning of the infusion, higher concentration of the drug in the tubing will be administered first and comprise the loading dose. This will be followed by exponentially decreasing infusion in the next phase, and in the final phase by the constant rate infusion with the concentration of the solution bag. In another alternative, however, the mixing vessel may be provided with a sufficiently high concentration of the drug to serve as the loading dose. The concentration may be adjusted, for example, so that 100 mg of lidocaine is administered in the first 10 minutes, at which time the concentration of lidocaine in the mixing vessel is 10 mg/ml. Administration will then continue at an exponentially decreasing rate down to lower concentration of the lidocaine in the solution bag, such as 2 mg/ml. Administration can then continue at the established low maintenance concentration, and, as required, additional solution bags can be attached with the drug at the same low maintenance concentration.

I claim:

1. Intravenous drug infusion apparatus for optimized drug delivery, comprising a closed container with a first sterile intravenously administerable aqueous carrier containing an intravenously administerable drug at a low maintenance concentration, said container having an outlet positionable at the bottom thereof for gravity outflow, a closed rigid mixing vessel of smaller volume than said container having therein a second sterile intravenously administerable aqueous carrier containing a high loading concentration of said drug, said mixing vessel having inlet means connected to said container outlet by conduit means, said inlet means terminating in a hollow needle having an inlet end communicating with the interior of said vessel, said needle being dimensioned and arranged to provide a turbulent mixing action in said vessel, said vessel having outlet means with its inner end spaced from said needle inlet end, the construction and arrangement of said inlet and outlet means providing the only mixing means associated with said vessel, and delivery conduit means connected to the outer end of said outlet means for intravenous delivery of the admixed carrier to a patient, said apparatus being adapted to deliver a close approximation of an exponentially decreasing concentration of said drug during the transition from said high loading concentration down to said low maintenance concentration.

2. The apparatus of claim 1 in which said drug is lidocaine.

3. The apparatus of claim 1 in which said drug is lidocaine and said carriers are normal saline solutions.

4. The apparatus of claim 1 in which said first carrier is supplied to said mixing vessel entirely by gravity flow.

5. Intravenous drug infusion apparatus for optimized drug delivery, comprising a closed container with a first sterile intravenously administerable aqueous carrier containing an intravenously administerable drug at a low maintenance concentration, said container having an outlet positionable at the bottom thereof for gravity outflow, a closed rigid mixing vessel of smaller volume than said container having therein a second sterile intravenously administerable carrier containing a high initial loading concentration of said drug, said loading concentration being at least three times that of said maintenance concentration, said first carrier having a volume at least five times that of said second carrier, said vessel having inlet means connected to said container outlet by conduit means, said inlet means providing a solution mixing action within said vessel, said vessel having outlet means positioned and arranged with respect to the inlet means so that mixing of said solutions can occur within said vessel for discharging an admixed solution to said outlet means, and delivery conduit means connected to the outer end of said outlet means for intravenous delivery of the admixed solution to a patient, said inlet means comprising a hollow needle having an inlet end extending into said vessel, said inlet needle being dimensioned and arranged to provide a turbulent mixing action in said vessel, said outlet means also comprising a hollow needle having its inner end located within said vessel in spaced-apart relation to the inlet end of said inlet needle, the construction and arrangement of said inlet and outlet needles providing the only mixing means associated with said vessel, said apparatus being adapted to deliver a close approximation of an exponentially decreasing concentration of said drug during the transition from said high loading concentration down to said low maintenance concentration.

6. The apparatus of claim 5 in which said drug is lidocaine.

7. The apparatus of claim 5 in which said drug is lidocaine and said carriers are normal saline solutions.

8. The apparatus of claim 5 in which said first carrier is supplied to said mixing vessel entirely by gravity flow.

9. The apparatus of claim 1 in which said hollow needle has an internal diameter no larger than a No. 27 hypodermic needle.

10. The apparatus of claim 5 in which said hollow inlet needle has an internal diameter no larger than a No. 27 hypodermic needle.

11. The apparatus of claim 1 in which pump means are interposed in the conduit means connecting the mixing vessel inlet means to said container outlet, said pump means being adapted to pass said first carrier to said mixing vessel at a preset rate.

12. The apparatus of claim 5 in which pump means are interposed in said conduit means connecting the mixing vessel inlet means to said container outlet, said pump means being adapted to pass said first carrier to said mixing vessel at a preset rate.

* * * * *